United States Patent [19]

Hill, Jr.

[11] Patent Number: 4,866,283
[45] Date of Patent: Sep. 12, 1989

[54] OPTICAL INSPECTION OF FOOD PRODUCTS

[75] Inventor: Ralph H. Hill, Jr., San Antonio, Tex.

[73] Assignee: Southwest Research Institute, San Antonio, Tex.

[21] Appl. No.: 231,258

[22] Filed: Aug. 12, 1988

[51] Int. Cl.[4] .................................. G01N 21/64
[52] U.S. Cl. ........................ 250/461.2; 250/459.1; 356/318; 209/578; 209/579
[58] Field of Search ............... 209/577, 578, 579, 581; 356/317, 318, 417; 250/461.1, 461.2, 458.1, 459.1

[56] References Cited

U.S. PATENT DOCUMENTS

| 4,203,522 | 5/1980 | Fraenkel et al. | 209/577 |
| 4,421,772 | 12/1983 | Munck et al. | 250/461.1 |
| 4,535,248 | 8/1985 | Schade et al. | 250/459.1 |

FOREIGN PATENT DOCUMENTS 993063  5/1965  United Kingdom ............ 250/461.2

Primary Examiner—Carolyn E. Fields
Attorney, Agent, or Firm—Matthews & Branscomb

[57] ABSTRACT

An optical inspection system for using laser-induced luminescence to detect the quality of organic materials, such as peanuts. The inspection system comprises an excitation means for illuminating a specimen to cause it to produce fluorescent radiation. The spectral representation of the fluorescence produced by the specimen is compared to a reference spectrum to obtain an indication of the physical characteristics of the specimen. In a preferred embodiment, the system identifies and removes peanuts contaminated with aflatoxin from a stream of peanuts by determining fluorescence at a predetermined wavelength.

10 Claims, 4 Drawing Sheets

OPTICAL INSPECTION OF FOOD PRODUCTS

FIELD OF THE INVENTION

The present invention relates generally to the field of optical inspection of materials. More specifically, the present invention provides a method and apparatus for utilizing laser-induced fluorescence techniques to determine the quality of organic materials, such as foods. The laser-induced fluorescence techniques of the present invention can be used to detect the existence of contaminants in a stream of materials containing desired food products, such as peanuts.

BACKGROUND

A common method of sorting food products is based on colorimetry. Food and biological samples have rather different light scattering properties than simple solids. The detection of slight variations in color, either by visual or by optical/electrical methods, can thus be used to sort the food products. One of the primary difficulties with such methods, however, is the inability to detect slight variations in color which represent different grades of the material or which represent undesired material. For example, in the case of food products such as peanuts, sorting systems which are based on colorimetry techniques often are not able to differentiate between a desired peanut and a rock or stem which may have the approximate color and size as a desired peanut.

In addition to the basic problem of differentiating between a desired peanut and a contaminant, such as a rock or stem, it is important to be able to locate and remove contaminated peanuts. One of the contaminants which food processors fear most is aflatoxin. This pervasive material, which is produced by the *Aspergillus flavus* fungus when food is improperly stored, costs the food industry millions of dollars per year. Current methods for detection of aflatoxin are time consuming and cumbersome.

For the reasons discussed above, it is apparent that there is a need for an effective inspection system for determining the quality of food products. In particular, there is a need for a system capable of differentiating between desired food products and contaminants which might not be apparent from a visual inspection of the material. The present invention overcomes the difficulties caused by standard color comparison techniques by providing an optical inspection system employing laser-induced fluorescence, as is discussed in greater detail below.

In order to understand the principles of operation of the present invention, it is important to understand the meaning of luminescence, as well as the historical evolution of the definition of luminescence. Historically, materials were said to exhibit characteristics of "luminescence" if they emitted photons after being irradiated with light having a wavelength in the range of approximately 1800 to 3700 Angstroms (ultraviolet). Prior art definitions of this phenomenom have included two categories: fluorescence and phosphorescence. A material was said to exhibit fluorescence if the luminescence ceased after termination of the irradiation. However, if the luminescence persisted after irradiation, the phenomena was termed phosphorescence.

The above-mentioned definitions evolved at a time when oboservations of the pesistence of luminescence were made with the unaided eye. The development of sophisticated instruments capable of measuring the persistance of luminescence for very short time periods, e.g., nanoseconds, as led to a more precise definition of the above-mentioned terms and has changed the definition of luminescence for some materials. For example, it is now known that many materials which have been characterized in the literature as being fluorescent emit luminescence for as long as 1000 microseconds after termination of excitation. This luminescence offers significant information regarding the physical characteristics of the illuminated material and in the present invention can be used to distinguish between desired food products and contaminants, as will be discussed in greater detail below.

It is well known that certain materials luminesce in the presence of ultraviolet or blue light and that the variations of the visible light luminescence can be used to determine certain features of the material. An example of an apparatus for using these phenomena to detect the presence of caries in human teeth is shown in U.S. Pat. Nos. 4,290,433 and 4,479,499 issued to Alfano. The luminescence in human teeth which is essential to the methods shown in these patents is dependent on the recognition of total visible luminescence. Further, the detection of the caries as shown therein relies on a visual recognition of differences in the color of the reradiated light from the teeth. While this luminescence technique is useful for detecting certain types of characteristics of materials, it is not suitable for an application such as that shown in the present invention because the technique is dependent on visual recognition of color differences in the luminescence of the material.

The invention method overcomes the shortcomings of pevious optical inspection systems because it takes advantage of complex excitation-luminescence spectra of peanuts. Thus, two objects which both reflect approximately the same spectrum can have different fluorescence characteristics which can be distinguished to differentiate between desired peanuts and contaminants.

SUMMARY OF THE INVENTION

The present invention provides a method of inspection and quality detection which can be used for sorting materials, particularly food products having a molecular composition which provides rapid fluorescence characteristics. The fluorescent radiation from a desired material has a specific characteristic spectrum which can be compared to and differentiated from the spectrum radiated from an undesired material. Through the use of laser-induced luminescence, or more particularly laser-induced fluorescence, it is possible to detect minor differences in the characteristics of the material which might not be detected using standard detection techniques.

The invention inspection and sorting system comprises an excitation source which illuminates the material to be examined in order to cause that material to produce fluorescent radiation. In a preferred embodiment of the invention, the excitation source is a laser. A light detection means is operable to detect the fluorescent light produced by the material under examination and is operable to produce a spectral representation of the fluorescent light produced by the material. This spectral representation is processed in a processing means capable of differentiating between the spectrum (or portion of the spectrum) of a desired material and that of an undesired material. An initial measurement of the fluorescent characteristics of a reference sample of the material is made using the above-mentioned system. The spectral response produced by the reference material is analyzed by the invention system and is stored in memory for subsequent comparisons with spectral responses of specimens of the food products, e.g., peanuts. in the present invention, the wavelength of excitation can be selected such that the contaminant does not fluoresce, or it can be selected such that a contaminant fluoresces at a different wavelength than the desired material. Such differentation is not possible with conventional fluorescence techniques, such as those based on the use of "black lights." Therefore, a black light could not be used to differentiate between food products, such as roasted peanuts, and contaminants.

The invention method for inspecting and sorting a material comprises the steps of illuminating the material with light from an excitation source, thereby causing the material to fluoresce; detecting the fluorescent light reradiated by the material and producing an output signal related to the spectrum in response thereto; processing the output signal to obtain a spectral representation of the reradiated light; and comparing the spectrum, or portion thereof, of the material under examination to the corresponding spectrum of a desired material.

DETAILED DESCRIPTION OF THE PREFERRED EMBODIMENT

Figure 1:
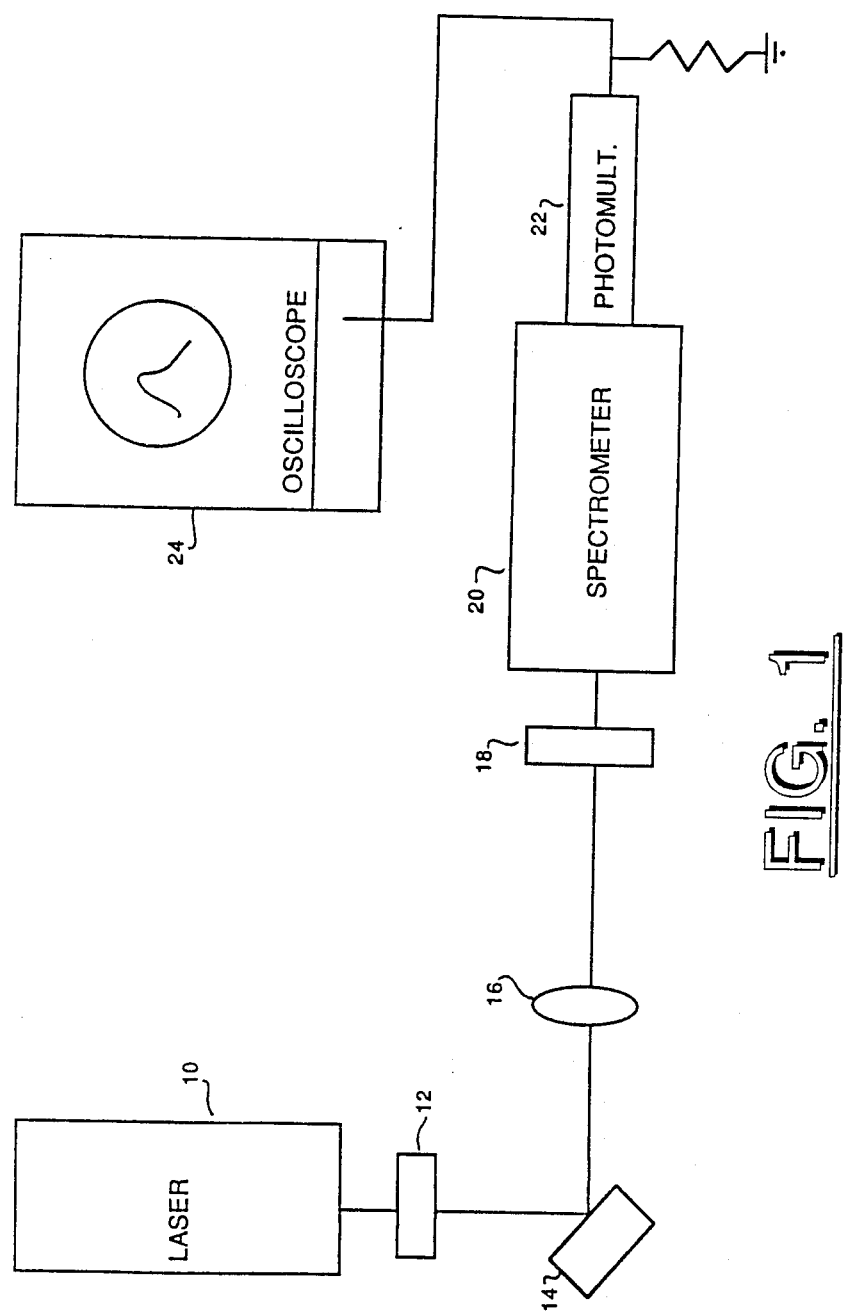
FIG. 1 is a schematic representation of the system configuration of the preferred embodiment used to measure total luminescence of a material as a function of time.

The preferred embodiment of the invention system for optical inspection of a food product is shown generally in FIGS. 1 through 4. Since the invention system is intended to be used with a wide variety of food products, it is necessary to make an initial determination of the fluorescence characteristics of the particular material using the system shown in FIGS. 1 & 2 to establish a reference spectral response for a particular food product to be tested. Once the reference fluorescence characteristics of the product have been determined, these characteristics can be stored and correlated with subsequent measurements. For this initial determination, light from an excitation source 10 is passed through a shutter 12 to illuminate a material 14 to be tested for fluorescence. In the preferred embodiment of the invention the excitation source 10 is a laser having a suitable wavelength to cause fluorescence. All subsequent discussion of the excitation source will refer generally to a laser. The shutter 12 of the system shown in FIG. 1 can be eliminanted if a pulsed laser is used.

The fluorescence characteristics of the test material are determined by analysis of the light reradiated by the sample. The reradiated light passes through lens 16, filter 18 and used as input for the spectrometer 20. The filter 18 can be selected to minimize the scattered light from the laser 10. The spectrometer 20 disperses the light which is then detected by the photomultiplier 22 and amplified to provide input for a suitable display device such as the oscilloscope 24 shown in FIG. 1.

Figure 2:
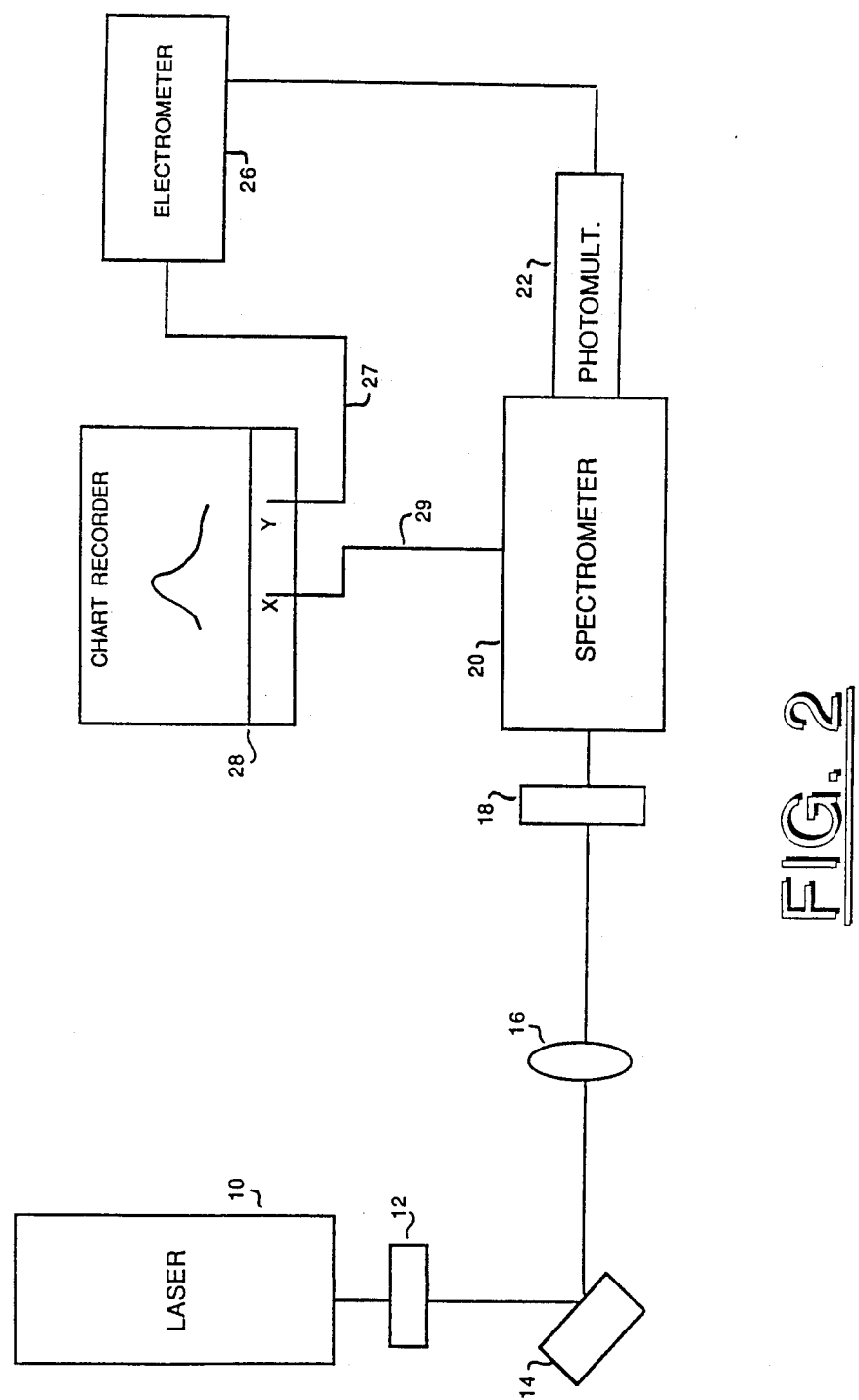
FIG. 2 is a schematic represenation of the system configuration of the preferred embodiment used to measure total luminescence of a material as a function of luminescent wavelength.

Those materials which exhibit the proper fluorescence characteristics can be tested for quality and sorted using the system shown in FIG. 2, which measures the total luminescence (fluorescence) as a function of wavelength. The system of FIG. 2 comprises many of the elements shown in FIG. 1. The output of the photomultiplier, however, is fed to an electrometer 26 which processes the signal provided by the photomultiplier to provide a fluorescent amplitude signal, illustrated by line 27, for input into the chart recorder 28, line 21 provides a wavelength reference signal for the chart recorder 28. Wavelength information is provided to the chart recorder by line 29.

Figure 3A:
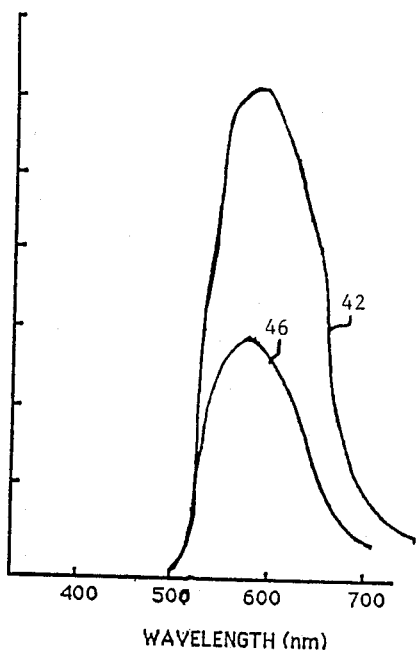
FIGS. 3A and 3B are graphical representations of luminescence amplitude of a material as a function of wavelength.
Figure 3B:
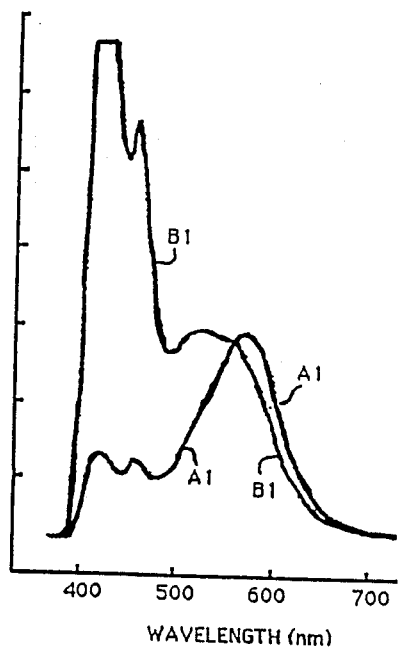

A typical output displayed on the chart recorder is shown in FIG. 3a. The upper curve 42 represents the spectrum observed for the desired material, while the lower curve 46 represents the spectrum observed for a material to be discarded. Alternatively, the system could be modified such that the upper curve could represent the discarded material, while the lower curve represents the desired material. The main requirement is that there must be difference between the observed spectra of the materials. FIG. 3b is a graphical illustration of actual data obtained by comparing the spectral response of a desired raw peanut and a raw peanut contaminated with aflatoxin using 363 nm excitation. In this figure the peanut contaminated with aflatoxin is denoted as A1 while the desired peanut is denoted as B1. As shown in the figure, the difference in amplitude beween the desired peanut and the contaminated peanut is maximum at about 425 nanometers, so this wavelength can be used for sorting.

Figure 4:
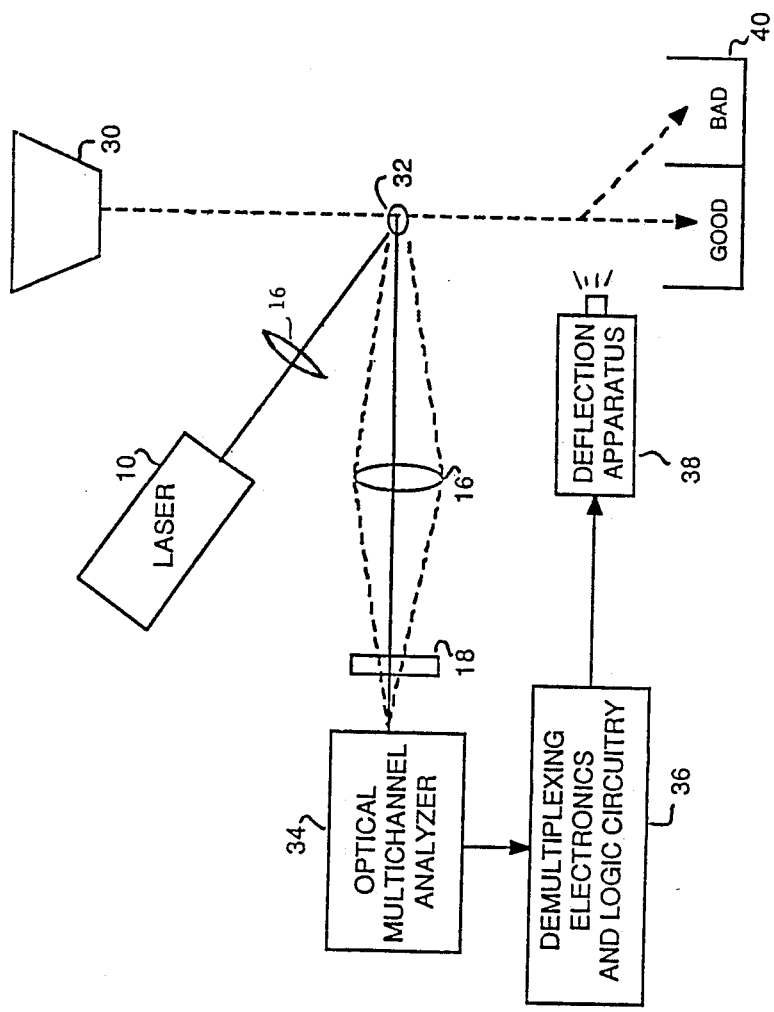
FIG. 4 is a schematic representation of a sorting system utilizing the luminescence detection system of the invention for sorting a material.

A system for employing the fluorescence spectra of the materials to be sorted is illustrated generally in FIG. 4. In this system, a storage bin 30 is adapted to store a large quantity of material 32 to be inspected and to pass a stream of the material past an inspection point. In the system shown, the materials fall past the inspection point due to gravity. As the material passes the inspection point, they are illuminated by an excitation beam from a laser 10, with appropriate optics, having a wavelength selected to cause fluorescence of the material, which wavelengths can be selected based on the results of tests performed on the specific material using the systems shown in FIGS. 1 and 2.

As the material passes the test point and is illuminated, it fluoresces thus providing a source of reradiated light which can be analyzed and processed to distinguish desired material from undesired material. In the system shown in FIG. 4, the fluorescence of the test material is fed into an optical multichannel analyzer 34 to be analyzed for spectral characteristics. Alternatively, a system of multiple detectors with filters could be used in place of the optical multichannel analyzer 34. The output of the optical multichannel analyzer 34 is processed by demultiplexing electronics and logic circuitry 36 to produce a signal representation of the spectral output of the material. An output signal is produced and used to control a deflection device 38 which allows desired material to fall into one portion of a bin 40, but which deflects undesired products into another bin. While a number of deflection devices could be used to perform this function, a compressed air source is used in the preferred embodiment.

One would not normally think of a peanut as a fluorescent material because, under standard room light conditions, the dominant process is simple light scattering and absorption. The wavelength dependence of these processes gives the peanut its characteristic color. Each photon of light is either absorbed or scattered by the peanut, but the wavelength remains essentially the same. Since room light contains all visible wavelengths, any fluorescence effects are completely masked. The desired flourescent effects can be observed, however, by illuminating the peanut with laser light at an appropriate wavelength, e.g., 488 nm, and looking at it through a filter that only passes longer wavelengths.

An experiment was performed utilizing the above-described system to sort roasted peanuts from contaminants. Peanuts are especially difficult to sort using conventional colorimetry techniques since they often are very close in color to rocks and other contaminants. Furthermore, peanuts produce very little or "almost no" fluorescent radiation under a conventional ultraviolet light. However, when peanuts are illuminated with light from an excitation source such as a laser, they produce a distinctive fluorescent radiation spectrum which can easily be differentiated from the spectrum of undesired materials. The results of this experiment show that laser-induced fluorescence can be used to differentiate peanuts from contaminants with a high degree of certainty. These experimental results indicate that argon ion laser excitation at 488 nm can be used with detection of fluorescence at 580 nm to implement this method.

As was mentioned above, the invention system is based on analysis of t he fluorescence spectrum of the material to be tested. Laser-induced luminescence is the emission of light resulting from the absorption of laser light by a substance. The wavelength of the reradiated light contains a major portion at the wavelength of the exciting laser light. However, it also contains many new wavelength components which are determined by the molecular structure of the absorbing material. The present invention is based on the discovery that peanuts have distinctive characteristic responses to radiation at certain frequencies. In particular, these characteristic responses can be used to differentiate between various grades of peanuts and can also be used to differentiate between desired peanuts and peanuts which are contaminated with aflatoxins.

For a given excitation spectrum, samples of a material can have different fluorescence or phosphorescence spectra, even though they appear visually similar. The method and apparatus of the present invention differs from standard ultraviolet fluorescence techniques in that it takes advantage of the complicated excitationluminescence spectra of the peanut.

While the method and apparatus of the present invention has been described in connection with the preferred embodiment, it is not intended to be limited to the specific form set forth herein but on the contrary, it is intended to cover such modifications, alternatives and equivalents as can reasonably be included within the scope and spirit of the invention as defined by the appended claims.

I claim:

1. A method for identifying and removing contaminants from a stream of materials containing peanuts, comprising the steps of:
    obtaining a reference spectral representation of laser-induced fluorescence produced by a desired peanut when irradiated with laser light having a first predetermined wavelength;
    exciting said stream of material with a source of laser light having said predetermined wavelength, causing desired peanuts in said stream to produce laser-induced fluorescence at a first amplitude at a second predetermined wavelength and causing contaminants in said stream to produce laser-induced fluorescence at a second amplitude at said second predetermined wavelength;
    detecting laser-induced fluorescence produced by said stream of material; correlating detected fluorescence at said first amplitude with desired peanuts in said stream of material and fluorescence at said second amplitude with contaminants in said stream of material; and
    removing said contaminants producing fluorescence at said second amplitude.

2. The method according to claim 1, said first predetermined wavelength of said laser light being approximately 488 nanometers.

3. The method according to claim 2, said second predetermined wavelength of said laser-induced fluorescence being approximately 580 nanometers.

4. The method according to claim 1, said first predetermined wavelength of said laser light being approximately 363 nanometers.

5. The method according to claim 4, said second predetermined wavelength of said laser-induced fluorescence being approximately 425 nanometers.

6. An optical system for the inspection of a stream of material containing peanuts, comprising:
    means for illuminating said stream of material with a quantity of laser light, said laser light having a predetermined wavelength for causing desired peanuts in said stream of material to produce laser-induced fluorescent radiation having a first amplitude at a second wavelength and causing contaminants in said stream of material to produce fluorescent radiation having a second amplitude at said second wavelength;
    means for detecting said laser-induced fluorescent radiation at said second wavelength and for producing an output data signal in response thereto, said data signal corresponding to the amplitude of said fluorescent radiation;
    means for correlating said output data signal with a reference data signal corresponding to a desired peanut and for generating a control signal upon detection fluorescent radiation at said second amplitude produced by said stream of material; and
    means responsive to said control signal for removing said contaminants from said stream of material.

7. The system according to claim 6, said laser light having a wavelength of approximately 488 nanometers.

8. The system according to claim 7, said second wavelength being approximately 580 nanometers.

9. The system according to claim 6, said laser light having a wavelength of approximately 363 nanometers.

10. The system according to claim 9, said second wavelength being approximately 425 nanometers.

* * * * *